United States Patent
Fortini et al.

(10) Patent No.: US 8,506,825 B2
(45) Date of Patent: Aug. 13, 2013

(54) METHOD AND APPARATUS FOR CONTROLLING THE FLOW RATE OF WASHING SOLUTION DURING THE WASHING STEP IN A BLOOD CENTRIFUGATION BOWL

(75) Inventors: Matteo Fortini, Corporeno (IT); Stefano Reggiani, Medolla (IT); Ivo Panzani, Mirandola (IT)

(73) Assignee: Sorin Group Italia S.r.l., Milan (IT)

( * ) Notice: Subject to any disclaimer, the term of this patent is extended or adjusted under 35 U.S.C. 154(b) by 880 days.

(21) Appl. No.: 11/604,664

(22) Filed: Nov. 27, 2006

(65) Prior Publication Data

US 2008/0124700 A1    May 29, 2008

(51) Int. Cl.
*B04B 1/00*    (2006.01)

(52) U.S. Cl.
USPC ........... 210/789; 210/782; 210/787; 210/739; 210/745; 494/1; 494/2; 494/5; 494/6; 494/10; 494/37; 494/43

(58) Field of Classification Search
USPC ................. 210/782, 787, 789, 790, 739, 745; 494/1, 2, 5, 6, 10, 37, 43; 435/2, 286.5
See application file for complete search history.

(56) References Cited

U.S. PATENT DOCUMENTS

| | | |
|---|---|---|
| 1,385,306 A | 7/1921 | Clayton |
| 2,835,517 A | 5/1958 | Beerli |
| 3,317,127 A | 5/1967 | Cole |
| 3,409,213 A | 11/1968 | Latham, Jr. |
| 3,565,330 A | 2/1971 | Latham, Jr. |
| 3,581,981 A | 6/1971 | Latham, Jr. |
| 3,785,549 A | 1/1974 | Latham, Jr. |
| 4,140,268 A | 2/1979 | Lacour |
| 4,668,214 A | 5/1987 | Reeder |
| 4,718,888 A | 1/1988 | Darnell |
| 4,795,419 A | 1/1989 | Yawn et al. |
| 4,838,849 A | 6/1989 | Calari |
| 4,889,524 A | 12/1989 | Fell et al. |
| 4,919,817 A | 4/1990 | Schoendorfer et al. |
| 5,060,957 A | 10/1991 | Stolzenberg et al. |
| 5,062,826 A | 11/1991 | Mantovani et al. |

(Continued)

FOREIGN PATENT DOCUMENTS

| EP | 0 682 953 A1 | 11/1995 |
|---|---|---|
| EP | 0 931 554 A2 | 7/1999 |

(Continued)

OTHER PUBLICATIONS

Gilbert et al., "Hematocrit Monitor," *Critical Care Medicine*, 17(9):929-933 (Sep. 1989).

(Continued)

*Primary Examiner* — John Kim
(74) *Attorney, Agent, or Firm* — Faegre Baker Daniels LLP

(57) ABSTRACT

A method of washing blood mixed with undesirable elements not normally found in healthy whole blood to remove the undesirable elements, the method comprising: separating the blood into components according to relative densities of the components with a rotating centrifuge bowl; providing a port through which fluid exits the bowl, the exiting fluid having a concentration of undesirable elements; flowing washing solution into the centrifuge bowl at an initial flow rate; monitoring the fluid exiting the bowl with an optical sensor having an output signal indicative of the composition of the exiting fluid; and increasing and decreasing the flow rate of the wash solution as a function of the output signal.

15 Claims, 3 Drawing Sheets

(56) References Cited

U.S. PATENT DOCUMENTS

| | | | |
|---|---|---|---|
| 5,104,372 A | 4/1992 | Rossetto |
| 5,288,088 A | 2/1994 | Santandrea et al. |
| 5,298,171 A | 3/1994 | Biesel |
| 5,311,908 A | 5/1994 | Barone et al. |
| 5,312,319 A | 5/1994 | Salter |
| 5,379,775 A | 1/1995 | Kruse |
| 5,383,911 A | 1/1995 | Mann |
| 5,385,539 A | 1/1995 | Maynard |
| 5,387,174 A | 2/1995 | Rochat |
| 5,417,715 A | 5/1995 | Noren et al. |
| 5,423,738 A | 6/1995 | Robinson et al. |
| 5,478,479 A | 12/1995 | Herrig |
| 5,505,683 A | 4/1996 | Geringer et al. |
| 5,591,113 A | 1/1997 | Darnell et al. |
| 5,607,579 A | 3/1997 | Latham, Jr. et al. |
| 5,658,231 A | 8/1997 | Schmitt et al. |
| 5,730,883 A | 3/1998 | Brown |
| 5,851,169 A | 12/1998 | Meresz et al. |
| 5,873,810 A | 2/1999 | Holm et al. |
| 5,876,611 A | 3/1999 | Shettigar |
| 5,919,125 A | 7/1999 | Berch |
| 5,964,690 A | 10/1999 | Patton et al. |
| 6,241,649 B1 | 6/2001 | Zanella et al. |
| 6,299,784 B1 | 10/2001 | Biesel |
| 6,348,031 B1 | 2/2002 | Unger et al. |
| 6,352,499 B1 | 3/2002 | Geigle |
| 6,416,456 B2 | 7/2002 | Zanella et al. |
| 6,605,028 B2 | 8/2003 | Dolecek |
| 6,629,919 B2 | 10/2003 | Egozy et al. |
| 6,716,151 B2 | 4/2004 | Panzani et al. |
| 7,001,323 B2 | 2/2006 | Panzani et al. |
| 7,452,322 B2 | 11/2008 | Headley et al. |
| 7,993,257 B2 | 8/2011 | Simonini et al. |
| 2003/0181305 A1 | 9/2003 | Briggs et al. |
| 2005/0054508 A1 | 3/2005 | Panzani et al. |
| 2006/0040818 A1 | 2/2006 | Jorgensen et al. |
| 2007/0213191 A1 | 9/2007 | Chammas |
| 2009/0305863 A1 | 12/2009 | Simonini et al. |
| 2011/0256999 A1 | 10/2011 | Simonini et al. |

FOREIGN PATENT DOCUMENTS

| | | |
|---|---|---|
| EP | 0 931 554 A3 | 7/1999 |
| EP | 1 254 675 A1 | 11/2002 |
| EP | 2138237 B1 | 12/2009 |
| JP | 09164343 A | 6/1997 |
| JP | 2005081087 A | 3/2005 |
| JP | 2009291335 A | 12/2009 |
| JP | 2010042398 A | 2/2010 |
| WO | WO 98/29149 | 7/1998 |

OTHER PUBLICATIONS

Steinke et al., "Role of Light Scattering in Whole Blood Oximetry," *IEEE Transactions on Biomedical Engineering*, BME-33(3):294-301 (Mar. 1986).

Zdrojkowski et al., "Optical Transmission and Reflection by Blood," *IEEE Transactions on Biomedical Engineering*, BME-17(2):122-128 (Apr. 1970).

European Search Report for counterpart EP Application No. 06 12 4795.3 (8 pages).

International Search Report for European Application No. 08157932, mailed Nov. 19, 2008, 4 pages.

METHOD AND APPARATUS FOR CONTROLLING THE FLOW RATE OF WASHING SOLUTION DURING THE WASHING STEP IN A BLOOD CENTRIFUGATION BOWL

FIELD OF THE INVENTION

This invention relates to a washing step in a blood centrifuge bowl for an autotransfusion system and in particular to a method and apparatus to control the rate of flow of washing solution during the washing step.

BACKGROUND OF THE INVENTION

It is known that in some medical procedures, such as inter- and postoperative autotransfusion, there is a need to collect or salvage the blood lost by the patient to make it available for reinfusion back into the patient. Prior to reinfusion, the collected or salvaged blood typically needs to be separated and washed to make the blood safer for the patient. Specifically, the red blood cells need to be separated from the plasma which contains high levels of undesired elements such as activated clotting proteins, anticoagulant, activated platelets, coagulation by-products, cellular debris and free hemoglobin (Hgb). The removal of the free Hgb is desirable because at high levels it is toxic and can cause kidney damage. The removal of cellular debris, such as broken cell membranes, is also desirable because it may cause blood clotting and/or kidney necrosis.

It is known that through an autotransfusion system the patient's blood can be recovered by devices that comprise a blood reservoir to collect the salvaged blood, a centrifuge bowl or cell, which separates, concentrates and washes the red blood cells from the other blood components, and a reinfusion pouch or bag in which the washed and concentrated red blood cells are made available for reinfusion to the patient.

It is known that the procedure for the separation of blood components is generally performed in centrifuge bowls and usually comprises three steps. The first step is generally known as the filling step and is performed by filling the centrifuge bowl through an inlet tube. The centrifugal force created by the rotation of the centrifuge bowl, causes the red blood cells, which are the heaviest cellular components of blood, to be propelled outward, compacting against the wall of the centrifuge bowl. Other cellular components such as white blood cells and platelets are arranged in a thin layer known as a buffy coat directly adjacent to the mass of compacted red blood cells. The separated plasma which contains the undesired elements is the remaining component of blood and is arranged in a layer which lies above the buffy coat. As filling continues, more and more of the heavier blood components, i.e. the red blood cells, are pushed upwardly along a circumferential wall of the bowl until the lighter plasma is discharged through an outlet at the top of the centrifuge bowl. Once the centrifuge bowl has substantially filled with red blood cells, the filling step ends and the introduction of new blood into the centrifuge bowl ceases.

The above-described filling step is followed by a washing step which is performed to remove plasma and other unwanted blood components that have become trapped between the red blood cells. This is accomplished by the passing of a washing solution, which is usually saline, into the centrifuge bowl. The washing solution, when introduced into the centrifuge bowl, is usually added at a steady flow rate and gradually takes the place of the plasma and other unwanted elements, thus expelling them from the centrifuge bowl. At the end of the washing step the centrifuge bowl contains mainly red blood cells and washing solution, i.e., substances suitable to be reinfused to the patient. The contents of the cell are collected in a reinfusion pouch or bag in a third step of the procedure, known as emptying. This reinfusion pouch can then be made available for reinfusion to the patient.

Proper control of the washing step is important to ensure that free Hgb and other undesirable components are adequately removed before the blood is reinfused into the patient. Although it is difficult to detect the presence or absence of cellular debris, anticoagulant and other undesirable elements in the salvaged blood, it is easy to detect the presence or absence of free Hgb due to its reddish color. Free Hgb levels are relatively easy to measure experimentally and free Hgb washout is proven to correlate well with washout of other undesirable elements. Therefore, it is common practice to concentrate on free Hgb washout in the salvaged blood since the other undesirable elements will also be washed out. U.S. Pat. No. 5,478,479 to Herrig describes a system that uses a free Hgb sensor in the waste line from the centrifuge bowl to monitor the level of free Hgb. Care must be used during the washing step to avoid the spilling of red blood cells (RBC's) into the waste line. The Herrig patent proposes to avoid RBC spilling by reducing the speed of the pump which pumps washing solution into the centrifuge bowl if the sensor in the waste line detects RBC's. See column 6, lines 12 to 19. However, Herrig does not suggest increasing the speed of the pump if the sensor does not detect RBC's. It would be desirable to have a method and apparatus which minimize RBC spilling and which optirmize the time and the quality of the global washing step.

SUMMARY OF THE INVENTION

The present invention provides a method and apparatus for optimizing the time and the quality of the washing step of an autotransfusion device while minimizing the amount of RBC's which are spilled.

The invention provides a method of washing blood mixed with undesirable elements not normally found in healthy whole blood to remove the undesirable elements, the method comprising: separating the blood into components according to relative densities of the components with a rotating centrifuge bowl; providing a port through which fluid exits the bowl, the exiting fluid having a concentration of undesirable elements; flowing washing solution into the centrifuge bowl at an initial flow rate; monitoring the fluid exiting the bowl with an optical sensor having an output signal indicative of the composition of the exiting fluid; and increasing and decreasing the flow rate of the wash solution as a function of the output signal.

The invention provides an apparatus for removing undesirable elements not normally found in healthy whole blood from blood mixed with the undesirable elements, the apparatus comprising: a rotatable centrifuge bowl for separating the blood into components according to relative densities of the components; a controllable pump for flowing washing solution into the centrifuge bowl; a port through which fluid exits the bowl; an optical sensor for monitoring the fluid exiting the bowl and generating an output signal indicative of the composition of the exiting fluid; and a controller operatively coupled to the pump for comparing the output signal with one or more predetermined values and causing the pump to increase, decrease, or hold constant the flow of washing solution into the centrifuge bowl.

Additional features and advantages of the invention are set forth in the description which follows and in part will be apparent from the description. The objectives and other advantages of the invention will be realized and attained by the method and apparatus as particularly pointed out in the written description and claims.

It is to be understood that both the foregoing general description and the following detailed description are exemplary and explanatory and are intended to provide further explanation of the invention as claimed.

BRIEF DESCRIPTION OF THE DRAWINGS

Further characteristics and advantages will become better apparent from the description of a preferred but not exclusive embodiment of the invention, illustrated by way of non-limiting example in the accompanying drawings.

DETAILED DESCRIPTION OF THE PREFERRED EMBODIMENTS

Figure 1:
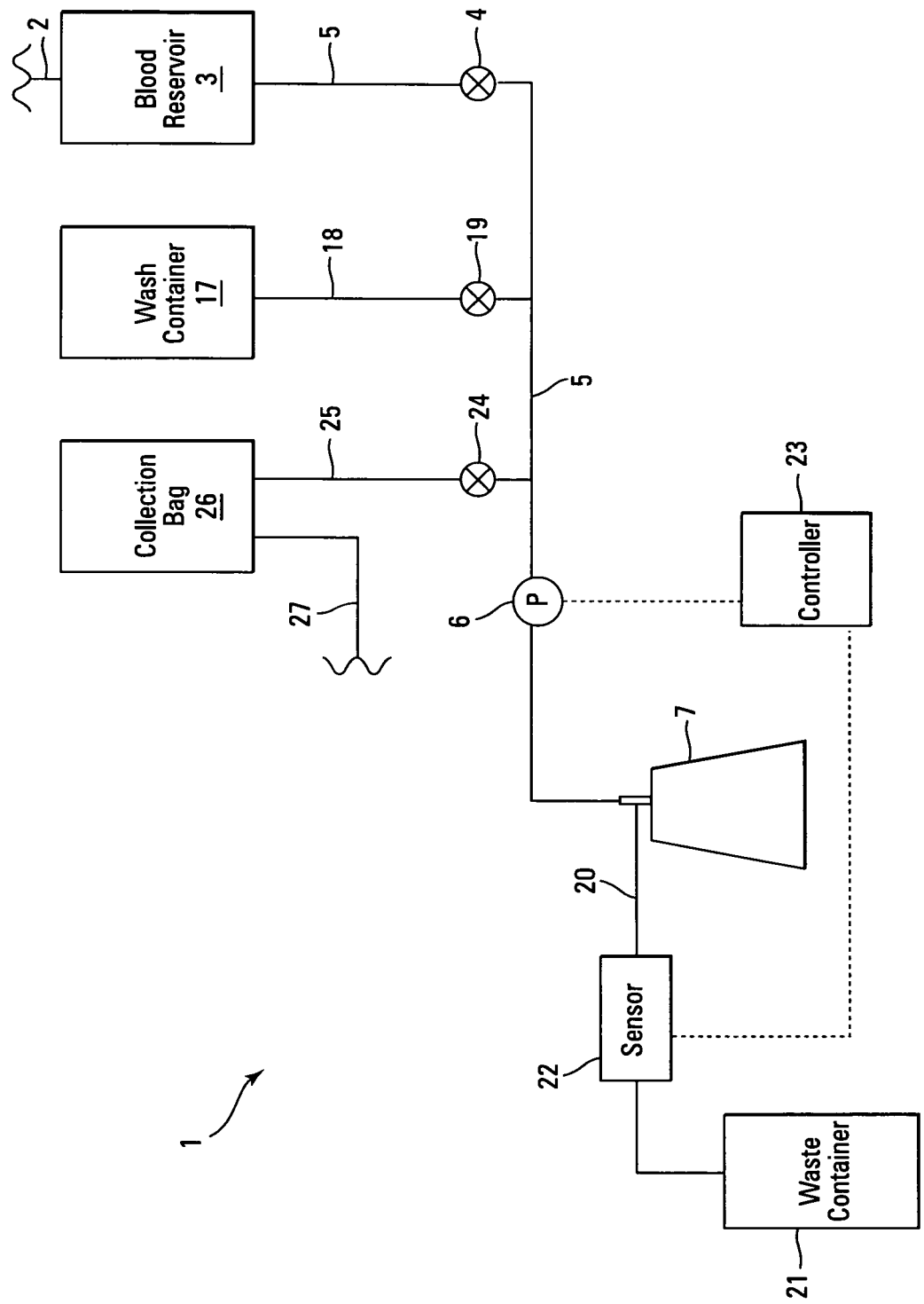
FIG. 1 is a schematic view of the present invention relating to a system to control the rate of flow of washing solution during the washing step.

The invention provides a method of washing blood mixed with undesirable elements not normally found in healthy whole blood to remove the undesirable elements, the method comprising: separating the blood into components according to relative densities of the components with a rotating centrifuge bowl; providing a port through which fluid exits the bowl, the exiting fluid having a concentration of undesirable elements; flowing washing solution into the centrifuge bowl at an initial flow rate; monitoring the fluid exiting the bowl with an optical sensor having an output signal indicative of the composition of the exiting fluid; and increasing and decreasing the flow rate of the wash solution as a function of the output signal. In one embodiment, the total time for the washing method is minimized while the hematocrit of the washed blood is held constant in comparison with the same method in which the flow rate is maintained at the initial rate. In another embodiment, the hematocrit of the washed blood is increased in comparison with the same method in which the flow rate is maintained at the initial rate.

In one embodiment, the flow rate of the washing solution is decreased if the optical sensor has an output signal indicative of slight red blood spilling into the exiting fluid. In another embodiment, the flow rate of the washing solution is increased if the optical sensor has an output signal indicative of no red blood spilling into the exiting fluid. In another embodiment, the flow rate of the washing solution is decreased to zero if the optical sensor has an output signal indicative of massive red blood spilling into the exiting fluid. The flow rate of the washing solution can be increased from zero after a certain amount of time.

In one embodiment, the flow rate of the washing solution is decreased if the optical sensor has an output signal indicative of slight red blood spilling into the exiting fluid, and the flow rate of the washing solution is increased if the optical sensor has an output signal indicative of no red blood spilling into the exiting fluid. In one embodiment, the flow rate of the washing solution is decreased if the optical sensor has an output signal indicative of slight red blood spilling into the exiting fluid, the flow rate of the washing solution is increased if the optical sensor has an output signal indicative of no red blood spilling into the exiting fluid, and the flow rate of the washing solution is reduced to zero if the optical sensor has an output signal indicative of massive red blood spilling into the exiting fluid.

In one embodiment, after a predetermined total volume of washing solution has been used, the output signal of the optical sensor is compared with a predetermined threshold value indicative of the amount of free Hgb in the exiting fluid. An additional amount of washing solution can be flowed into the centrifuge bowl if the output signal does not meet the threshold value indicative of the amount of free Hgb in the exiting fluid.

The optical sensor can measure the transmission of light or the reflection of light. In one embodiment, the optical sensor measures light having a wavelength in the range from 530 to 580 nm. In another embodiment, the optical sensor measures light having a wavelength of 565 nm. In one embodiment, the optical sensor comprises a light emitting diode. In another embodiment, the optical sensor measures only one wavelength of light.

In one embodiment, the undesirable elements comprise at least one of free Hgb, cellular debris, clotting proteins, activated platelets, coagulation byproducts, and anticoagulant. In another embodiment, the undesirable elements comprise free Hgb.

In one embodiment, the method further comprises reinfusing at least one of the components into the patient. In another embodiment, the washing solution is a saline solution.

The invention provides an apparatus for removing undesirable elements not normally found in healthy whole blood from blood mixed with the undesirable elements, the apparatus comprising: a rotatable centrifuge bowl for separating the blood into components according to relative densities of the components; a controllable pump for flowing washing solution into the centrifuge bowl; a port through which fluid exits the bowl; an optical sensor for monitoring the fluid exiting the bowl and generating an output signal indicative of the composition of the exiting fluid; and a controller operatively coupled to the pump for comparing the output signal with one or more predetermined values and causing the pump to increase, decrease, or hold constant the flow of washing solution into the centrifuge bowl. In one embodiment, the apparatus further comprises a container for reinfusing at least one of the components into a patient. In another embodiment, the apparatus further comprises a port for admitting blood into the bowl.

In one embodiment, the optical sensor comprises a light source and a light detector, the light source emitting light which passes through the fluid exiting the bowl and the detector receiving the light after it passes through the fluid. In another embodiment, the optical sensor comprises a light source and a light detector, the light source emitting light which contacts the fluid exiting the bowl and the detector receiving the light after it is reflected by the fluid. In another embodiment, the optical sensor measures light having a wavelength in the range from 530 to 580 nm. In one embodiment, the optical sensor measures light having a wavelength of 565 nm. In one embodiment, the optical sensor comprises a light emitting diode. In another embodiment, the optical sensor measures only one wavelength of light.

In one embodiment, the controller causes the pump to decrease the flow rate of the washing solution if the optical sensor has an output signal indicative of slight red blood spilling into the exiting fluid. In another embodiment, the controller causes the pump to increase the flow rate of the washing solution if the optical sensor has an output signal indicative of no red blood spilling into the exiting fluid. In one embodiment, the controller causes the pump to decrease to zero the flow rate of the washing solution if the optical sensor has an output signal indicative of massive red blood spilling into the exiting fluid. The controller can cause the pump to increase from zero the flow rate of the washing solution after a certain amount of time.

In one embodiment, the controller causes the pump to decrease the flow rate of the washing solution if the optical sensor has an output signal indicative of slight red blood spilling into the exiting fluid, and the controller causes the pump to increase the flow rate of the washing solution if the optical sensor has an output signal indicative of no red blood spilling into the exiting fluid. In another embodiment, the controller causes the pump to decrease the flow rate of the washing solution if the optical sensor has an output signal indicative of slight red blood spilling into the exiting fluid, the controller causes the pump to increase the flow rate of the washing solution if the optical sensor has an output signal indicative of no red blood spilling into the exiting fluid, and the controller causes the pump to decrease to zero the flow rate of the washing solution if the optical sensor has an output signal indicative of massive red blood spilling into the exiting fluid.

In one embodiment, after a predetermined total volume of washing solution has been used the controller compares the output signal of the optical sensor with a predetermined threshold value indicative of the amount of free Hgb in the exiting fluid. The controller can cause the pump to flow an additional amount of washing solution into the centrifuge bowl if the output signal does not meet the threshold value indicative of the amount of free Hgb in the exiting fluid.

Referring to FIG. 1, autotransfusion system 1 includes an inlet line 2 for suctioning salvaged blood lost from an operation field of a patient, or other blood source (not shown). Inlet line 2 carries the suctioned blood from the operation field to blood reservoir 3. The salvaged blood in blood reservoir 3 is pumped through line 5 and valve 4 and into centrifuge bowl 7 by pump 6. As the salvaged blood is pumped into the centrifuge bowl valve 4 is open and valve 19 and valve 24 are closed. Centrifuge bowl 7 could also be configured to receive blood directly from the operation field. Centrifuge bowl 7 separates and washes the salvaged blood received from blood reservoir 3. Washing solution, for washing the blood in the centrifuge bowl, is contained in wash container 17, and is pumped into the centrifuge bowl by pump 6 through line 18, valve 19, and line 5. Waste container 21, used for collecting waste fluid from the salvaged blood as it is processed in the centrifuge bowl, is connected to centrifuge bowl 7 by waste line 20. Waste line 20 is coupled to sensor 22, which senses the absorption of an LED output of the passing waste fluid from the centrifuge bowl to the waste container. The sensor 22 can measure light transmitted through waste line 20 or reflected back from waste line 20. The LED has a wavelength of 565 nm. The Hgb molecule absorbs in the wavelength range of 530 to 580 nm. The resulting attenuation is directly correlated to the amount of Hgb in the fluid. For a transmission sensor, Hgb that is still contained in RBC's will attenuate (increase for reflection sensors) the light much more than free Hgb. However, the apparatus is not used as a quantitative measurement of the Hgb/RBC's level, but as a sensor of the process behavior. Considering the case of a transmission Hgb sensor, the attenuation is expected to decrease steadily up to a plateau during the wash phase, the plateau meaning almost complete removal being reached. The controller monitors the relative changes to the signal. A steady or increasing signal represents a normal wash behavior, a decreasing signal represents either a transient worsening of the wash phase (small decrease: <80% or <90% compared to the previous sample) or RBC spillage (large decrease: <70% compared to the previous sample).

Sensor 22 sends continuous signals to controller 23. The signals which are sent to the controller indicate the amount, if any, of red blood cells perceived to be spilling into the waste fluid. Controller 23 processes the information received from sensor 22 and uses the processed information to control the speed of pump 6 and thus the rate of flow of the washing solution. Centrifuge bowl 7 is connected to collection bag 26, through line 5, valve 24 and line 25 which collects the washed blood and stores it for reinfusion back to the patient. Line 27 allows the washed blood collected in collection bag 26 to be transferred back to the patient if so desired.

Figure 2:
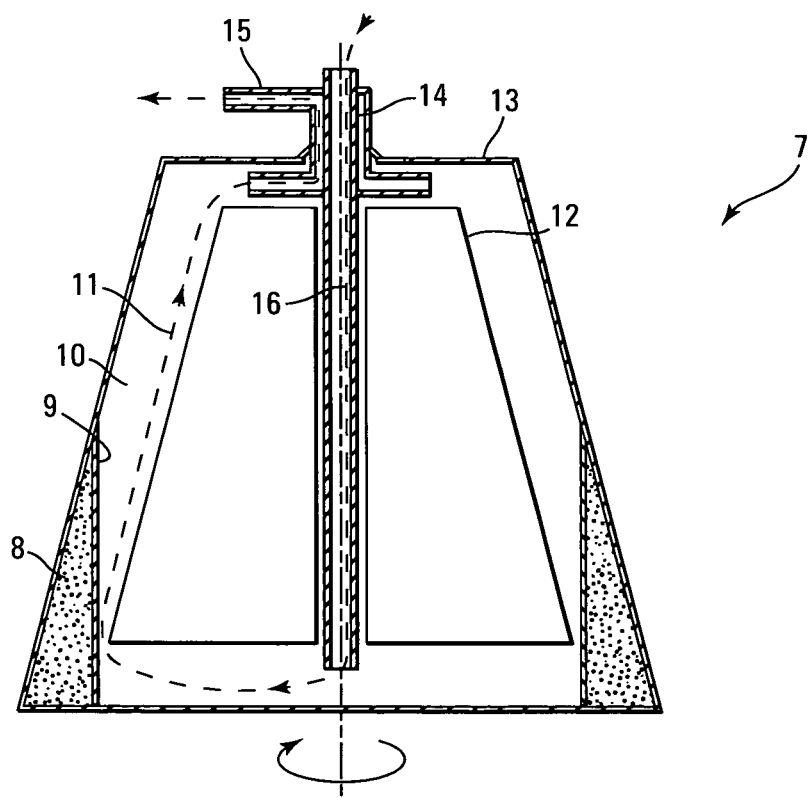
FIG. 2 is a schematic view of a blood centrifuge bowl.

Referring now to FIG. 2, centrifuge bowl 7 comprises inner bell 12 and outer bell 13 which are mutually rigidly coupled and are made to rotate. Blood entering the centrifuge bowl follows path 16 through inlet chamber 14 and into separation chamber 10 between the inner and outer bells. Centrifugation separates the blood components by the rotation of a motor that creates a centrifugal force causing the blood within separation chamber 10 to separate into different fractions in accordance with each blood component's density. The centrifugal force causes red blood cells 8, which are the higher density components of blood, to be propelled outward, compacting against the wall of the centrifuge bowl. Intermediate density blood components such as white blood cells and platelets are arranged in a thin layer known as a buffy coat 9, directly adjacent to the mass of compacted red blood cells. Lower density blood components such as plasma, which contains some of undesired elements such as free Hgb, are the remaining components and are arranged in a layer which lies above buffy coat 9. As the filling of the centrifuge bowl continues, the higher density components push the lighter density blood components upwards and closer to a rotation axis of the centrifuge bowl, thus the lighter density components are eventually displaced out of the centrifuge bowl following path 11 through outlet chamber 15 and then through waste line 20 and into waste container 21. The blood components and fluid displaced through waste line 20 will herein be referred to as waste fluid. Once the centrifuge bowl has substantially filled with red blood cells, as indicated by a sensing mechanism usually located within the centrifuge well, the space between inner bell 12 and outer bell 13, the filling step ends and the introduction of new blood into the centrifuge bowl ceases. A washing step, which washes the remaining blood, is then initiated to eliminate the plasma and other unwanted blood components that remain in the centrifuge bowl and that have become trapped between the red blood cells.

Figure 3:
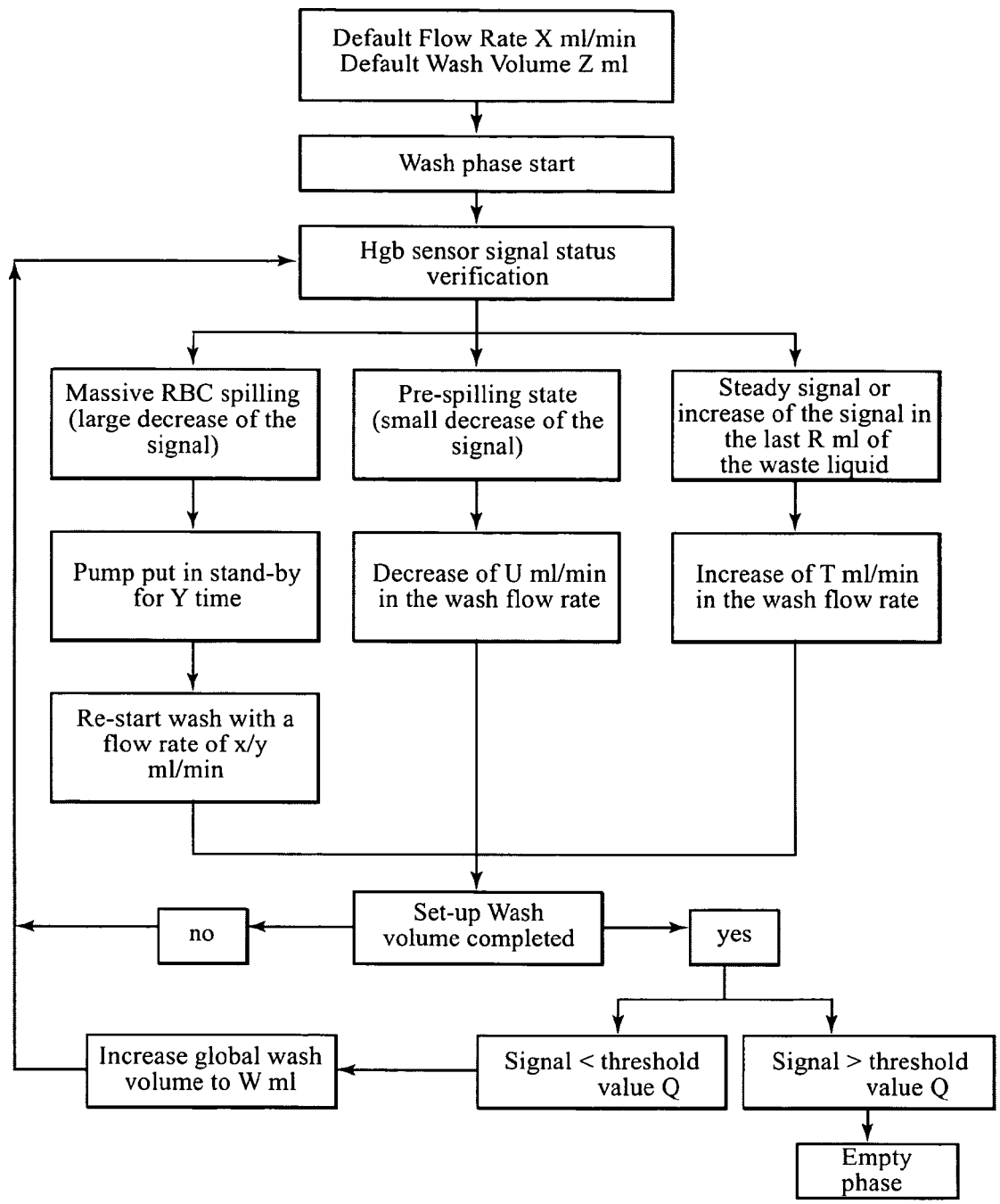
FIG. 3 is a flow chart of one embodiment of the present invention for controlling the rate of flow of the washing solution during the washing step.

A feedback driven control system of the present invention for optimizing the washing step is shown in the flow chart of FIG. 3. The steps set forth in FIG. 3 can be implemented by software, firmware, or hardware depending on system design. For purposes of the present invention the term "optimizing the washing step" means reducing the washing time and/or increasing the quality of the final blood product. The washing step, which is initiated by controller 23, begins at a default flow rate of X ml/min and a global default wash volume of Z ml. The default flow rate is automatically chosen by the machine, considering the bowl size and the filling program. A typical range is 100 to 600 ml/min, but the operator could manually change the setpoint value. The global default washing volume is automatically chosen by the machine, considering the bowl size and the filling program, but it could be manually modified by the user. Typical values are 300 to 1500 ml. Controller 23 is in communication with pump 6 and sensor 22, which begins sensing the absorption of the LED output by the fluid in the waste line upon initiation of the washing step and continues sensing until the global default wash volume Z is reached. The washing solution, an example being physiological saline solution (0.9 g/L NaCl in water), is pumped from wash container 17, into centrifuge bowl 7 by the pump 6, through line 18, valve 19, and line 5. As the washing solution is pumped into the centrifuge bowl, valve 4 and valve 24 are closed and valve 19 is open. The washing solution enters the centrifuge bowl and flows through and washes the blood components gradually expelling the lighter density blood components out through waste line 20 and into waste container 21. As the waste fluid flows through waste line 20, sensor 22, which is in communication with controller 23, senses the absorption of the LED output by the waste fluid and sends a signal to the controller indicating the sensed amount of RBC spillage in the waste fluid. In the case of a transmission Hgb sensor, a steady or increasing sensor output signal is indicative of negligible RBC spillage in the waste fluid. An abruptly decreasing sensor output signal is indicative of the presence of a high level of RBC spillage in the waste fluid.

In the flow chart shown in FIG. 3 there are three possible situations which can be encountered depending on the level of the sensor signal.

In a first situation, sensor 22 communicates to controller 23 a steady or relative increase of the signal in the last R ml of waste fluid volume that has passed through the sensor. A typical value for R is 40 to 60 ml. The value for R can be programmed or selected by the user. This signal is indicative of negligible RBC spillage and a high wash quality. In this first situation the controller signals to pump 6 to increase the wash flow rate T ml/min which decreases the overall global wash time S while maintaining the high quality of the wash. A typical value for T is 25 ml/min. The value for T can be programmed or selected by the user.

In a second situation, sensor 22 communicates to controller 23 a slight relative decrease of the signal (<80% or <90% compared to the previous sample) in the last 1 ml of waste fluid volume that has passed through the sensor. This signal is indicative of pre-RBC spilling. Pre-RBC spilling means that the RBC compaction is not broken, but the washing solution is slowly eroding it. Continuing to do so will either break the RBC wall and cause spilling, or remove enough RBC's to recover to a stable situation. In this second situation the controller signals to pump 6 to decrease the wash flow rate by U ml/min to avoid RBC spilling and to enhance or preserve the high quality of the wash and overall hematocrit (hct) %. A typical value for U is 50 ml/min. The value for U can be programmed or selected by the user.

In a third situation, sensor 22 communicates to controller 23 a large decrease of the signal in the last 1 ml of waste fluid volume that has passed through the sensor. This is indicative of massive RBC spilling. In this third situation the controller signals pump 6 to standby for a time Y while the centrifuge bowl continues rotating. A typical time Y is in the range of 1 to 30 seconds. After time Y has passed, the wash step is restarted with a flow rate of x/y ml/min, where x is the flow rate before the pump was stopped and y is a number greater than 1 so that x/y is less than x. A typical value for y is 4/3. The value for y can be programmed or selected by the user.

This feedback driven system providing control of the washing step based on the sensor signal possibilities described above continues until the global default wash volume Z is reached. Thus, during a single washing step, the flow rate of the washing solution may have increased, decreased, or stopped depending on the level of the sensor signal.

Other control algorithms could be used. One could tune a classical control system that has an always increasing input summed to the error function, which would force it to look for the maximum flow. A classical control which will try to reach an increasing first derivative of the quality can be used. Other control algorithms, such as fuzzy logic ones, can be used and could give a more fine-tuned control.

Further, the amount of increase (T ml/min) or decrease (U ml/min) can be fixed or can be variable depending on the intensity of the sensor signal.

The global wash volume could be increased, if at the end of the Z ml, the liquid waste quality is not considered acceptable, for example, based on a signal that is lower then a desired threshold value Q. The value Q is user selected, but there is a default value of 60%. This process preferably is automated. If the liquid waste quality is not considered acceptable, the global wash volume is increased automatically to W ml, in steps of 100 ml, until the signal increases above the predetermined threshold Q or until a wash volume of 1.5 Z has been reached. When the washing step is completed, the emptying step is initiated by controller 23 whereby the washed blood remaining in centrifuge bowl 7 is reverse pumped into collection bag 26 through line 5, valve 24 and line 25 by pump 6. As the washed blood is pumped out of the centrifuge bowl, valve 4 and valve 19 are closed while valve 24 is open. The washed blood collected from the centrifuge bowl in collection bag 26 can be stored for later use or can be reinfused into patient directly through line 27.

Experiments have been conducted comparing outlet hematocrit, total procedure time, average wash flow rate and sensor average signal intensity of the feedback driven washing step control system described above with a standard wash step using a steady wash flow rate. The sensor average signal intensity is the average sensor signal intensity over the entire procedure time.

The results of two experiments using bovine blood are set forth below.

| | Experiment 1<br>Bowl size: 55 ml<br>Inlet Hct: 24% | |
|---|---|---|
| | Standard Wash | Feedback-Driven System |
| Outlet Hct (%) | 47 | 48 |
| Procedure time (seconds) | 303 | 195 |
| Average wash flow rate (ml/min) | 100 | 257 |
| Sensor average signal (mV) | 832 | 795 |

As the results indicate, the feedback driven control system results in a considerable decrease in the procedure time (>35%) while maintaining approximately the same wash quality (as indicated by the average sensor signal and % hct).

| | Experiment 2<br>Bowl size: 125 ml<br>Inlet Hct: 24% | |
|---|---|---|
| | Standard Wash | Feedback-Driven System |
| Outlet Hct (%) | 57 | 59 |
| Procedure time (seconds) | 403 | 648 |

-continued

Experiment 2
Bowl size: 125 ml
Inlet Hct: 24%

|  | Standard Wash | Feedback-Driven System |
|---|---|---|
| Average wash flow rate (ml/min) | 250 | 175 |
| Sensor average signal (mV) | 302 | 702 |

In this experiment a high buffy coat level was used for the purpose of increasing outlet Hct. As the results show the feedback driven control system was able to considerably decrease RBC spilling (as evidenced by comparison of the average sensor signals) while reaching an even higher outlet Hct level. In this case the high quality washing step results with low RBC spillage were achieved by the feedback driven control system by decreasing the average wash flow rate and increasing the procedure time.

The above description and accompanying drawings are provided for the purpose of describing embodiments of the invention and are not intended to limit the scope of the invention in any way. It will be apparent to those skilled in the art that various modifications and variations can be made in the devices and methods without departing from the spirit or scope of the invention. Thus, it is intended that the present invention cover the modifications and variations of this invention provided they come within the scope of the appended claims and their equivalents.

What is claimed is:

1. A method of washing blood mixed with undesirable elements not normally found in healthy whole blood to remove the undesirable elements, the method comprising:
   separating the blood into components according to relative densities of the components with a rotating centrifuge bowl;
   allowing fluid to exit the bowl through a port, the exiting fluid having a concentration of undesirable elements;
   setting an initial flow rate of washing solution in accordance with a size of the centrifuge bowl;
   flowing washing solution into the centrifuge bowl at the initial flow rate;
   monitoring the fluid exiting the bowl with an optical sensor having an output signal indicative of the composition of the exiting fluid; and
   increasing the flow rate of the washing solution relative to the initial flow rate if the optical sensor has an output signal indicative of no red blood cells spilling into the exit fluid;
   decreasing the flow rate of the wash solution relative to the initial flow rate if the optical sensor has an output signal indicative of slight red blood cell spilling into the exit fluid as a function of the output signal,
   decreasing the flow rate of the washing solution to zero for a period of time if the optical sensor has an output signal indicative of massive red blood cells spilling into the exiting fluid; and
   restarting the washing solution after the period of time has passed.

2. The method of claim 1, wherein the total time for the washing method is minimized while the hematocrit of the washed blood is held constant in comparison with the same method in which the flow rate is maintained at the initial rate.

3. The method of claim 1, wherein the hematocrit of the washed blood is increased in comparison with the same method in which the flow rate is maintained at the initial rate.

4. The method of claim 1, wherein after a predetermined total volume of washing solution has been used, the output signal of the optical sensor is compared with a predetermined threshold value indicative of the amount of free Hgb in the exiting fluid.

5. The method of claim 4, wherein an additional amount of washing solution is flowed into the centrifuge bowl if the output signal does not meet the threshold value indicative of the amount of free Hgb in the exiting fluid.

6. The method of claim 1, wherein the optical sensor measures the transmission of light.

7. The method of claim 1, wherein the optical sensor measures the reflection of light.

8. The method of claim 1, wherein the optical sensor measures light having a wavelength in the range from 530 to 580 nm.

9. The method of claim 8, wherein the optical sensor measures light having a wavelength of 565 nm.

10. The method of claim 1, wherein the optical sensor comprises a light emitting diode.

11. The method of claim 1, wherein the optical sensor measures only one wavelength of light.

12. The method of claim 1, wherein the undesirable elements comprise at least one of free Hgb, cellular debris, clotting proteins, activated platelets, coagulation byproducts, and anticoagulant.

13. The method of claim 12, wherein the undesirable elements comprise free Hgb.

14. The method of claim 1, further comprising reinfusing at least one of the components into the patient.

15. The method of claim 1, wherein the washing solution is a saline solution.

* * * * *